United States Patent [19]

Lorz et al.

[11] Patent Number: 5,202,297
[45] Date of Patent: Apr. 13, 1993

[54] RHODIUM HYDROFORMYLATION CATALYSTS CONTAINING BISPHOSPHITE LIGANDS

[75] Inventors: Peter M. Lorz, Mannheim; Werner Bertleff, Viernheim; Michael Roeper, Wachenheim; Dieter Koeffer, Weinheim, all of Fed. Rep. of Germany

[73] Assignee: Basf Aktiengesellschaft, Ludwigshafen, Fed. Rep. of Germany

[21] Appl. No.: 747,596

[22] Filed: Aug. 20, 1991

[30] Foreign Application Priority Data

Aug. 21, 1990 [DE] Fed. Rep. of Germany ....... 4026406

[51] Int. Cl.$^5$ .................................................. B01J 31/24
[52] U.S. Cl. ....................................... 502/106; 502/161; 556/13; 556/16; 556/18; 558/76; 568/454
[58] Field of Search .................. 502/166, 161; 556/13, 556/16, 18

[56] References Cited

U.S. PATENT DOCUMENTS 3,952,045  4/1976  Gaenzler .............................. 260/463

FOREIGN PATENT DOCUMENTS 0096988  12/1983  European Pat. Off. .
0149894  7/1985  European Pat. Off. .
0155508  9/1985  European Pat. Off. .
0213639  3/1987  European Pat. Off. .
0214622  3/1987  European Pat. Off. .
096986  4/1987  European Pat. Off. .
0353770  2/1990  European Pat. Off. .
2236856  2/1975  France .

OTHER PUBLICATIONS

Journal Chem. Research (S), 1980, Asymmetric Catalyses, Part 111 . . . Brunner at al. p. 76.
Organometallies 1988, 7, 33–37, Synthesis and Complexation of a New Chealting Bis(phosphite) . . . Bleeke et al.
Inorg. Chem. 1990, 29 5006–5008, Practical Synthese of Cheisting . . . , Wink et al.

Primary Examiner—Patrick P. Garvin
Attorney, Agent, or Firm—Herbert B. Keil

[57] ABSTRACT

Rhodium hydroformylation catalysts containing bisphosphite ligands of the formula I

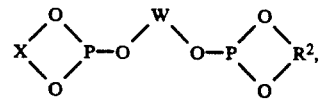

where
—X— is a divalent bisarylene radical or $R^1$,
W is a divalent arylene, bisarylene or alkylene radical, and
$R^1$ and $R^2$ are identical or different and are substituted or unsubstituted alkylene or ortho-arylene.

6 Claims, No Drawings

RHODIUM HYDROFORMYLATION CATALYSTS CONTAINING BISPHOSPHITE LIGANDS

The present invention relates to rhodium catalysts containing specific bisphosphites as ligands, and to their use in hydroformylation.

For the purposes of the present invention, carbonylation reactions are the production of oxygen-containing products by reacting an organic compound with carbon monoxide and preferably a further reactant, in particular hydrogen, in the presence of a catalyst. A particularly important reaction in industry is the hydroformylation of olefins by reaction with carbon monoxide and hydrogen to form aldehydes which contain one carbon atom more than the starting materials. The catalysts used are group VIII transition-metal complexes with phosphorus-containing ligands, for example phosphines (see J. Falbe, New Syntheses with Carbon Monoxide, Springer Verlag, New York 1980).

Besides cobalt catalysts, rhodium catalysts for the hydroformylation of lower alpha-olefins have become increasingly important in recent years since they allow the reaction to be carried out at lower pressures. The phosphorus ligand used is generally an excess of triphenylphosphine; a high ligand:rhodium ratio is necessary to increase the selectivity of the reaction for the commercially desired n-aldehyde product.

In recent years, attempts have been made to find more highly effective phosphorus ligands for hydroformylation. In addition to phosphines with various substituents, phosphites have also been studied for suitability as catalysts. In coordination compounds around a transition-metal center, phosphites give catalysts of increased activity, but the service life of these catalyst systems is unsatisfactory due to the high sensitivity to hydrolysis of the phosphite ligands. It is reported that chelating polyphosphites which are substituted by bisaryldiols, as described in EP-A-214 622, have drastically reduced sensitivity to hydrolysis, and the rhodium complexes of these ligands form extremely active hydroformylation catalysts. EP-A-213 639 describes bisphosphite chelates which contain a diorganophosphite function on one phosphorus atom and a triorganophosphite function on the second. Furthermore, EP-A-155 508 discloses the use of bisaryldiol-substituted monophosphites in the rhodium-catalyzed hydroformylation of sterically hindered olefins, for example isobutene.

Finally, diol- and triol-substituted monophosphites and their use in hydroformylation are described in EP-A2-149 894, EP-A2-096 988 and EP-A2-096 986.

Although said bisphosphites are very good complex ligands for rhodium hydroformylation catalysts, it is an object of the present invention to further improve their effectiveness and resistance to hydrolysis.

We have found that this object is achieved by improved rhodium hydroformylation catalysts containing bisphosphite ligands of the formula I

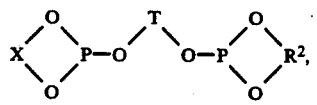

where
—X— is a divalent bisarylene radical or $R^1$,

T is a divalent arylene, bisarylene or alkylene radical, and $R^1$ and $R^2$ are identical or different and are substituted or unsubstituted alkylene or ortho-arylene.

Preferred compounds of the formula 1 are those in which X and T in the formula I are bisarylene, in particular the radical of the formula II

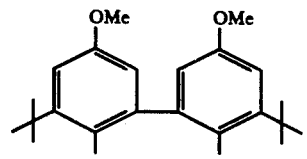

and $R^2$ is o-phenylene, 2,2-dimethyl-1,3-propylene or 1,1,2,2-tetramethylethylene. Furthermore, compounds of the formula I which should be emphasized are those in which W, $R^1$ and $R^2$, independently of one another, are o-phenylene, 2,2-dimethyl-1,3-propylene or 1,1,2,2-tetramethylethylene.

Symmetric compounds, ie. those in which X and $R^2$ are identical, are preferred since they are particularly easy to prepare.

The bisphosphites to be used according to the invention can be prepared by conventional methods through a suitable sequence of phosphorus halide/alcohol condensation reactions.

(a) For example, phosphorus trichloride is reacted with a diol to form a monochlorophosphite;

(b) this intermediate is reacted with a further diol to form the corresponding hydroxyl-substituted diorganophosphite;

(c) this diorganophosphite intermediate is reacted with phosphorus trichloride to form the corresponding phosphorus dichloride intermediate;

(d) and finally this dichloride is reacted with an appropriate diol to form the desired bisphosphite.

While this synthetic route is necessary for the preparation of asymmetrically substituted phosphites, symmetrically substituted compounds can be prepared by reacting the product of step (a) with an appropriate diol in the molar ratio 2:1.

Said condensation reactions are generally carried out in a suitable solvent, for example toluene, in the presence of an auxiliary base, for example triethylamine, as HCl acceptor.

The bisphosphite ligands prepared in this way are highly suitable for the preparation of rhodium complexes for carbonylation reactions, particularly for hydroformylation. They have high stability to hydrolysis and, in particular in combination with rhodium as the catalyst metal, a high catalytic activity. Due to their high molecular weight, they have low volatility and can therefore readily be separated from the highly volatile reaction products. They are readily soluble in all common organic solvents. They are particularly suitable for the hydroformylation of alpha- and internal olefins, including isobutene, and, depending on the phosphite employed, aldehydes can be produced with varying selectivity, from low to high proportions of the n-product.

The bisphosphite ligands of this invention are employed both as ligands of group VIII transition-metal complexes and as free phosphorus ligands which are preferably present in the reaction medium. Neither is it necessary for the phosphorus ligand of the group VIII transition-metal bisphosphite complex and the excess free ligand to be identical, although this is generally the case. Furthermore, mixtures of different ligands can be present as the free ligand component. The hydroformylation process can be carried out using any excess of free bisphosphite ligands; however, the presence of free bisphosphite ligands is not absolutely necessary.

In general, from about 2 to 100 mol, preferably from 3 to 50 mol, of ligand are employed per mol of the group VIII transition metal, ie. the sum of complexed and free ligands. Fresh ligand may be added at any point during the reaction in order to keep the concentration of free ligand constant. The transition-metal bisphosphite complex catalysts may be synthesized in advance, but the catalytically active complexes are generally formed in the reaction medium from a catalyst precursor, such as $Rh(CO)_2$(acetylacetonate), $Rh_2O_3$, $Rh_4(CO)_{12}$, $Rh_6(CO)_{16}$, $Rh(NO_3)_2$ or $Rh(OAc)_2$, and the bisphosphite ligand. The rhodium component employed is preferably $Rh(CO)_2$(acetylacetonate) or $Rh(OAc)_2$, and is reacted with the bisphosphite ligand in the presence of a solvent in order to form the precursor of the catalytically active complex, which is introduced into the reactor together with excess ligand in order to react in situ under the reaction conditions to give the active catalyst.

The concentration of the group VIII complex catalyst is generally from 10 to 1,000 ppm, calculated as the free metal, preferably from 10 to 500 ppm, in particular from 25 to 350 ppm of Rh. The olefins to be hydroformylated may be terminally or internally unsaturated, straight-chain, branched or cyclic. They may contain from 2 to 20 carbon atoms and also a plurality of ethylenically unsaturated groups.

The carbonylation and preferably hydroformylation is generally carried out in an organic solvent (which is inert under the reaction conditions) for the group VIII transition-metal complex. The amount of solvent is not crucial and need only be sufficient to dissolve the necessary amount of rhodium in the reaction medium.

The hydroformylation in the presence of the novel phosphites is carried out at from 30° to 200° C. and at from 0.05 to 700 bar.

In general, the use of the novel bisphosphites results in a reduction in the reaction temperature necessary. In the hydroformylation of olefins, the preferred pressure is less than 100 bar or, better still, less than 35 bar. The minimum pressure is determined principally by the total amount of reactants necessary to maintain the reaction.

In general, the $H_2$:CO molar ratio is from 1:10 to 100:1 or more, but preferably from 1:1 to 40:1. The reaction temperature should be from 20° to 200° C., but in general from 30° to 130° C.

The hydroformylation of alpha-olefins is preferably carried out at from 40° to 130° C., while less-reactive olefins, such as isobutene and internal olefins, or mixtures of alpha-olefins and internal olefins, are hydroformylated at from 50° to 130° C.

The bisphosphites to be used according to the invention may be additionally stabilized by adding to the hydroformylation medium an arylthiol of the formula ArSH where Ar is a substituted or unsubstituted aryl group.

The examples below are intended to illustrate the present invention.

EXAMPLE 1

Propene was hydroformylated in the presence of a mixture of $Rh(CO)_2$(acetylacetonate) and the bisphosphite ligand of the formula (1) in 100 ml of Texanol® in a 300 ml autoclave stirred magnetically, under the following reaction conditions: 90 ppm of rhodium, 70° C., 10 bar of CO:$H_2$ (molar ratio 1:1), total pressure 30 bar, 4 hours, 1.0 mol of propene. The reaction products were analyzed by gas chromatography.

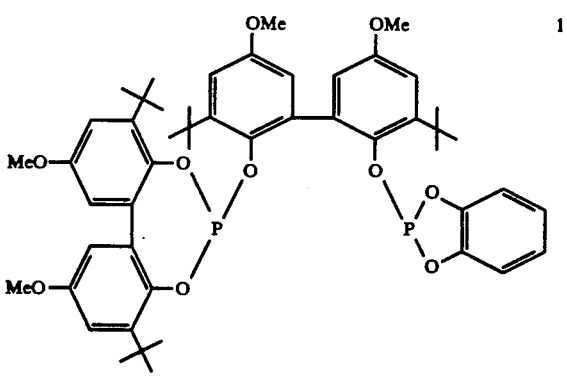

At an L/Rh ratio of 5.0 (mol/mol), a yield of butyraldehyde of 96% with an n-content of 59% was obtained.

The bisphosphite ligand (1) was synthesized as follows:

From a mixture of 10.0 g (28 mmol) of 2,2'-dihydroxy-3,3'-di-tert-butyl-5,5'-dimethoxy -1,1'-biphenyl and 400 ml of toluene, water was removed azeotropically by distilling off 70 ml of toluene; 39 ml (280 mmol) of triethylamine were added to the resultant solution, and the mixture was added dropwise over the course of 1 hour at −20° C. to a solution of 3.9 g (28 mmol) of phosphorus trichloride in 100 ml of toluene. The mixture was subsequently warmed to room temperature, stirred for 1 hour and refluxed for 2 hours. 10.0 g (28 mmol) of 2,2'-dihydroxy-3,3'-di-tert-butyl-5,5'-dimethoxy-1,1'-biphenyl and 39 ml (280 mmol) of triethylamine in 200 ml of toluene were added dropwise over the course of 30 minutes at −20° C. to this reaction mixture. The mixture was slowly warmed to room temperature and refluxed for 4 hours. 3.9 g (28 mmol) of phosphorus trichloride in 50 ml of toluene were subsequently added dropwise. The mixture was stirred at room temperature for 1 hour and then refluxed for 2 hours. Finally, 3.1 g (28 mmol) of 1,2-dihydroxybenzene and 39 ml (280 mmol) of triethylamine in 200 ml of toluene were added dropwise over the course of 30 minutes at −20° C. The mixture was stirred at room temperature for 1 hour and refluxed for 5 hours.

The reaction mixture was filtered while hot, and the clear filtrate was freed from solvent under reduced pressure. The residue was extracted twice with 50 ml of acetonitrile in each case. The white product remaining was (1) (melting point: 207° C.), which could be isolated in a yield of 58%. The structural proposal for 1 was $^{31}$P-NMR data (CDCl$_3$: $\delta_1$=138 ppm, $\delta_2$=141 ppm. The chemical shift was determined externally against $H_3PO_4$.

EXAMPLE 2

Propene was hydroformylated in the presence of a mixture of $Rh(CO)_2$(acetylacetonate) and the bisphosphite ligand of the formula (2) in 100 ml of Texanol® in a 300 ml autoclave stirred magnetically, under reaction conditions corresponding to those of Example 1. The reaction products were analyzed by gas chromatography.

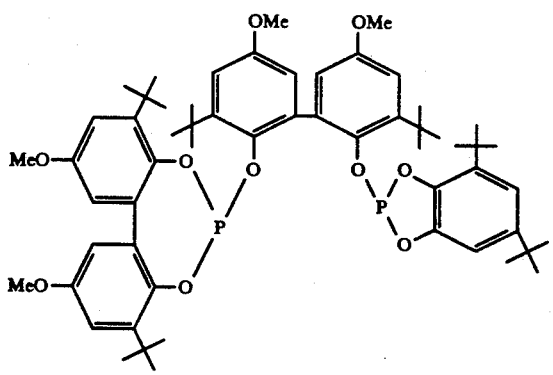

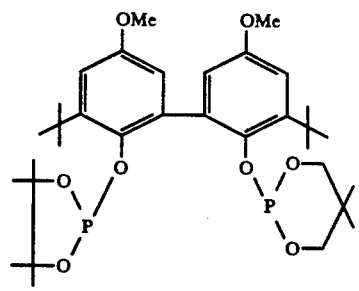

At an L/Rh ratio of 4.8 (mol/mol), a yield of butyraldehyde of 95% with an n-content of 66% was obtained.

The bisphosphite ligand (2) was synthesized as follows:

From a mixture of 35.8 g (0.1 mol) of 2,2'-dihydroxy-3,3'-di-tert-butyl-5,5'-dimethoxy-1,1'-biphenyl and 500 ml of toluene, water was removed azeotropically by distilling off 75 ml of toluene; 140 ml (1.0 mol) of triethylamine were added to the solution, and the mixture was added dropwise over the course of 30 minutes at −40° C. to a solution of 13.8 g (0.1 mol) of phosphorus trichloride in 1 l of toluene. The mixture was slowly warmed and stirred (1 hour) at room temperature and then refluxed for 3 hours. A solution of 35.8 g (0.1 mol) of 2,2'-dihydroxy-3,3'-di-tert-butyl-5,5'-dimethoxy-1,1'-biphenyl and 70 ml (0.5 mol) of triethylamine in 500 ml of toluene was added to this mixture over the course of 30 minutes at −20° C. The mixture was warmed to room temperature and refluxed for 3 hours. 13.8 g (0.1 mol) of phosphorus trichloride in 100 ml of toluene were then added over the course of 30 minutes at −20° C. The mixture was warmed to room temperature and subsequently refluxed for 1 hour. 22.2 g (0.1 mol) of 1,2-dihydroxy-3,5-di-tert-butylbenzene and 140 ml (1.0 mol) of triethylamine in 450 ml of toluene were added over the course of 30 minutes at −20° C. The mixture was warmed to room temperature and then refluxed for 3 hours.

The reaction mixture was filtered while hot, and the clear filtrate was freed from solvent under reduced pressure. The residue was dissolved in 500 ml of hot acetonitrile, and the solution was filtered while hot. On cooling, (2) crystallized as a white solid (melting point: 162° C.), which could be isolated in a yield of 60%.

$^{31}$P-NMR (CDCl$_3$):$\delta_1$=141 ppm, $\delta_2$=142 ppm. The chemical shift was determined externally against H$_3$PO$_4$.

EXAMPLE 3

Propene was hydroformylated in the presence of a mixture of Rh(CO)$_2$(acetylacetonate) and the bisphosphite ligand of the formula (3) in 100 ml of Texanol ® in a 300 ml autoclave stirred magnetically, under reaction conditions corresponding to those of Example 1. The reaction products were analyzed by gas chromatography.

At an L/Rh ratio of 4.1 (mol/mol), a yield of butyraldehyde of 81% with an n-content of 91% was obtained.

The bisphosphite ligand was synthesized as follows:

13 g (0.11 mol) of 2,3-dimethyl-2,3-butanediol were taken up in 400 ml of toluene, and 100 ml of toluene were distilled off for azeotropic drying. 154 ml (1.1 mol) of triethylamine were added, and the solution was added dropwise over the course of 30 minutes at −40° C. to 15.1 g (0.11 mol) of phosphorus trichloride dissolved in 1 l of toluene. The mixture was subsequently warmed to room temperature and refluxed for 1.5 hours. 39.4 g (0.11 mol) of 2,2'-dihydroxy-3,3'-di-tert-butyl-5,5'-dimethoxy-1,1'-biphenyl and 77 ml (0.55 mol) of triethylamine in 450 ml of toluene were added over the course of 1 hour at −40° C., and the mixture was warmed to room temperature and refluxed for 3 hours. 15.1 g (0.11 mol) of phosphorus trichloride in 500 ml of toluene were subsequently added over the course of 0.5 hour at −40° C. The mixture was warmed to room temperature and then refluxed for 4 hours. After cooling to −40° C., 1.4 g (0.11 mol) of 2,2-dimethyl-1,3-propanediol and 154 ml (1.1 mol) of triethylamine in 400 ml of toluene were added dropwise (0.5 hour) to the reaction mixture. The mixture was warmed to room temperature, refluxed for 4 hours and filtered while hot, and the clear filtrate was freed from solvent under reduced pressure. The residue was extracted with 250 ml of acetonitrile. The white solid remaining was (3), which could be isolated in a yield of 47% (melting point: 158° C.).

$^{31}$O-NMR data (CDCD$_3$):$\delta_1$=118 ppm, $\delta_2$=142 ppm. the chemical shift was determined externally against H$_3$PO$_4$.

EXAMPLE 4

Propene was hydroformylated in the presence of a mixture of Rh(CO)$_2$(acetylacetonate) and the bisphosphite ligand of the formula (4) in 100 ml of Texanol ® in a 300 ml autoclave stirred magnetically, under reaction conditions corresponding to those of Example 1. The reaction products were analyzed by gas chromatography.

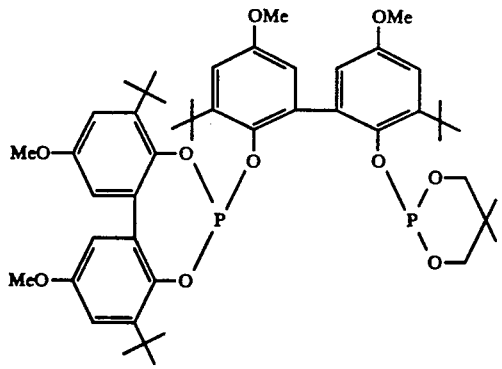

4

At an L/Rh ratio of 4.9 (mol/mol), a yield of butyraldehyde of 94% with an n-content of 68% was obtained.

The bisphosphite ligand (4) was synthesized as follows:

A solution of 71.6 g (0.2 mol) of 2,2'-dihydroxy-3,3'-di-toluene was dried azeotropically by distilling off 75 ml of toluene, 280 ml (2.0 mol) of triethylamine were then added, and the mixture was added dropwise over the course of 20 minutes at −30° C. to a solution of 27.5 g (0.2 mol) of phosphorus trichloride in 1 l of toluene. The mixture was warmed to room temperature and then refluxed for 3 hours. 71.6 g (0.2 mol) of 2,2'-dihydroxy-3,3'-di-tert-butyl-5,5'-dimethoxy-1,1'-biphenyl and 140 ml (1.0 mol) of triethylamine in 400 ml of toluene were subsequently added to the mixture over the course of 20 minutes at −20° C., and the mixture was warmed to room temperature and refluxed for 3 hours. After cooling to −25° C., 27.5 g (0.2 mol) of phosphorus trichloride in 100 ml of toluene were added dropwise over the course of 10 minutes. The mixture was warmed to room temperature and then refluxed for 2 hours. 20.8 g (0.2 mol) of 2,2-dimethyl-1,3-propanediol and 280 ml (2.0 mol) of triethylamine in 400 ml of toluene were then added dropwise over the course of 10 minutes at −20° C. The mixture was warmed to room temperature, refluxed for 2.5 hours and filtered while hot, and the clear filtrate was freed from solvent under reduced pressure. The residue was dissolved in 1 l of hot acetonitrile and filtered; on cooling, (4) crystallized as a white solid (melting point: 210° C.) (yield: 70%).

$^{31}$P-NMR data (CDCl$_3$): $\delta_1 = 120$ ppm, $\delta_2 = 142$ ppm. The chemical shift was determined externally against H$_3$PO$_4$.

EXAMPLES 5 and 6

The bisphosphite ligands 5 and 6 were employed as described in Example 1 in the batchwise hydroformylation of propene.

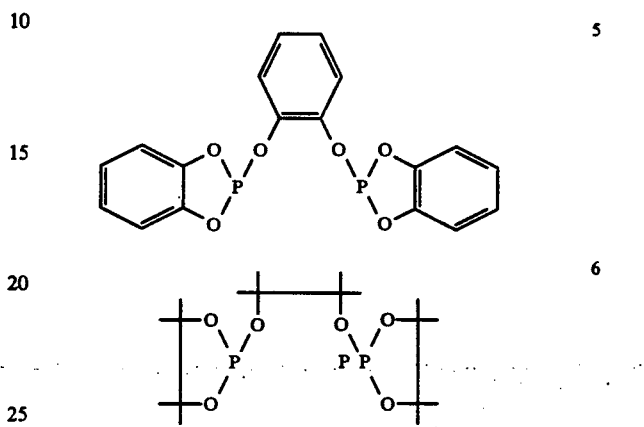

The reaction conditions and results are given in Table 1. The reaction products were analyzed by gas chromatography.

TABLE 1

| Ligand | L/Rh ratio (mol/mol) | Yield of BA (%) | n-content (%) |
|---|---|---|---|
| 5 | 4.7 | 99 | 60 |
| 6 | 4.9 | 97 | 71 |

Reaction conditions: 90 ppm of Rh, 100° C., 10 bar of CO:H$_2$ (molar ratio 1:1), total pressure 45 bar, 4 hours, 1.0 mol of propene, 100 ml of Texanol ®

COMPARATIVE EXAMPLE

This example demonstrates the catalystic activity of two bisphosphites described in EP-A-214 622 as hydroformylation catalysts and synthesized and tested for comparison purposes. The experiment was carried out as described in Example 2.

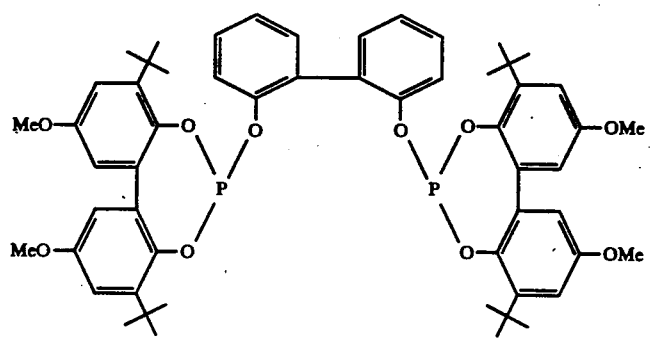

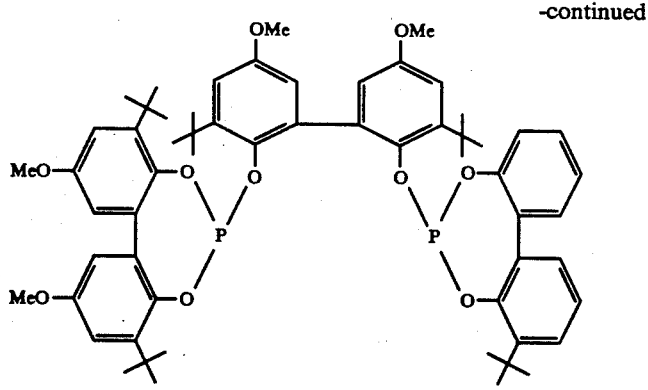

8

The reaction conditions and results are given in Table 2. The reaction products were analyzed by gas chromatography.

TABLE 2

| Ligand | L/Rh ratio (mol/mol) | Yield of BA (%) | n-content (%) |
| --- | --- | --- | --- |
| 7 | 3.5 | 82 | 58 |
| 8 | 5.1 | 86 | 91 |

Reaction conditions: 90 ppm of rhodium, 70° C., 10 bar of $CO:H_2$ (molar ratio 1:1), total pressure 30 bar, 4 hours, 1.0 mol of propene, 100 ml of Texanol ®

EXAMPLE 7

Propene was hydroformylated continuously by feeding a carbon monoxide/hydrogen gas mixture, hydrogen and circulation gas to an experimental reactor in such an amount that, at a constant 475 l/h of circulation gas and 30 l/h of offgas, the carbon monoxide content in the circulation gas was from 4 to 5% by volume. The liquid discharge from the reactor was decompressed, and the aldehyde product was separated off in a falling-film evaporator. The catalyst-containing bottom product was recycled continuously into the reactor. The catalyst employed was the bisphosphite (1) of Example 1.

The results and reaction conditions are given in Table 3. The reaction products were analyzed by gas chromatography.

TABLE 3

| t (d) | Propene (g/h) | Conversion (%) | BA yield (%) | n-content (%) | space-time yield (g/l · h) | propane yield (%) | Rh (ppm) |
| --- | --- | --- | --- | --- | --- | --- | --- |
| 1 | 165 | 98 | 90 | 85 | 240 | 0.9 | 142 |
| 2 | 188 | 99 | 91 | 84 | 278 | 0.5 | |
| 3 | 184 | 99 | 94 | 83 | 281 | 0.6 | |
| 4 | 218 | 99 | 94 | 86 | 330 | 0.9 | |
| 5 | 215 | 99 | 93 | 87 | 323 | 1.2 | |
| 6 | 217 | 99 | 93 | 88 | 325 | 1.2 | |
| 7 | 214 | 99 | 93 | 88 | 321 | 1.5 | 127 |

Reaction conditions: solvent Texanol ® and butyraldehyde, 4.14 mmol of Rh as $[Rh(OAc)_2]_2$, 36.5 g (41.4 mmol) of bisphosphite (1), L/Rh ratio=10:1 (mol/mol), T=60°−70° C., P=20 bar, circulation gas: 475 l/h, offgas: 30 l/h, catalyst recycling: 600 ml/h.

EXAMPLE 8

The experiment was carried out as in Example 7. The ligand employed was the bisphosphite 2. The carbon monoxide content in the circulation gas was from 13 to 14% by volume. The results and reaction conditions are given in Table 4. The reaction products were analyzed by gas chromatography.

TABLE 4

| t (d) | Propene (g/h) | Conversion (%) | BA yield (%) | n-content (%) | space-time yield (g/l · h) | propane yield (%) | Rh (ppm) |
| --- | --- | --- | --- | --- | --- | --- | --- |
| 1 | 235 | 98 | 92 | 72 | 349 | 2.6 | 131 |
| 2 | 235 | 98 | 94 | 74 | 355 | 1.7 | — |
| 3 | 236 | 99 | 96 | 72 | 367 | 0.8 | — |
| 4 | 233 | 98 | 95 | 73 | 358 | 1.5 | — |
| 5 | 232 | 98 | 94 | 74 | 353 | 2.2 | — |
| 6 | 234 | 98 | 92 | 75 | 346 | 2.5 | — |

Reaction conditions: solvent Texanol ® and butyraldehyde, 4.14 mmol of Rh as $[Rh(OAc)_2]_2$, 41.2 g (41.4 mmol) of bisphosphite (2), L/Rh ratio=10:1 (mol/mol), T=70°14 80° C., p=20 bar, circulation gas: 475 l/h, offgas: 30 l/h, catalyst recycling: 600 l/h.

COMPARATIVE EXAMPLE

This example demonstrates the catalytic activity of the bisphosphite 8 described in EP-A-214 622.

The experiment was carried out as in Example 6. The carbon monoxide content in the circulation gas was from 4 to 5% by volume. The results and reaction conditions are given in Table 5. The reaction products were analyzed by gas chromatography.

TABLE 5

| t (d) | Propene (g/h) | Conversion (%) | BA yield (%) | n-content (%) | space-time yield (g/l · h) | propane yield (%) | Rh (ppm) |
| --- | --- | --- | --- | --- | --- | --- | --- |
| 1 | 230 | 93 | 83 | 96 | 310 | 2.7 | 130 |
| 2 | 229 | 94 | 84 | 96 | 310 | 2.7 | — |
| 3 | 228 | 94 | 83 | 96 | 304 | 2.9 | — |
| 4 | 231 | 94 | 81 | 96 | 304 | 2.9 | — |
| 5 | 234 | 93 | 82 | 96 | 308 | 2.8 | — |
| 6 | 231 | 94 | 82 | 96 | 307 | 2.7 | — |

Reaction conditions: solvent Texanol ® and butyraldehyde, 4.14 mmol of Rh as $[Rh(OAc)_2]_2$, 15.9 g (16.56 mmol) of bisphosphite (8), L/Rh ratio=4.0:1 (mol/mol), T=90°−95° C., p=20 bar, circulation gas: 475 l/h, offgas: 30 l/h, catalyst recycling: 600 ml/h.

EXAMPLE 9

The bisphosphite ligands 1 to 4 were employed as described in Example 1 in the batchwise hydroformylation of trans-2-butene. The reaction conditions and results are given in Table 6. The reaction products were analyzed by gas chromatography.

TABLE 6

| Ligand | L/Rh ratio (mol/mol) | Yield (pentanal) (%) | n-content (%) |
|---|---|---|---|
| 1 | 4.8 | 91 | 41 |
| 2 | 4.9 | 89 | 52 |
| 3 | 4.8 | 51 | 31 |
| 4 | 4.9 | 58 | 35 |

Reaction conditions: 90 ppm of Rh, 90° C., 13 bar of CO:H$_2$ (molar ratio 1:1), total pressure 25 bar, 4 hours, 1.0 mol of trans-2-butene, 90 ml of Texanol ®.

COMPARATIVE EXAMPLE

This example demonstrates the catalytic activity of the bisphosphite 8 described in EP-A-214 622 as a hydroformylation catalyst and synthesized and tested for comparative purposes.

The reaction conditions and the results are given in Table 7. The reaction products were analyzed by gas chromatography.

TABLE 7

| Ligand | L/Rh ratio (mol/mol) | Yield (pentanal) (%) | n-content (%) |
|---|---|---|---|
| 8 | 4.7 | 31 | 37 |

Reaction conditions: 90 ppm of Rh, 90° C., 13 bar of CO:H$_2$ (molar ratio 1:1), total pressure 25 bar, 4 hours, 1.0 mol of trans-2-butene, 90 ml of Texanol ®.

We claim:

1. A rhodium hydroformylation catalyst containing bisphosphite ligands of the formula I

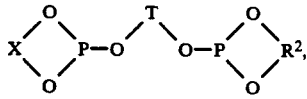   I where

—X— is a divalent bisarylene radical or R$^1$,

T is a divalent arylene or bisarylene radical, and

R$^1$ and R$^2$ are identical or different and are hydrocarbyl substituted or unsubstituted alkylene or ortho-arylene.

2. A rhodium hydroformylation catalyst containing bisphosphite ligands of the formula I as defined in claim 1, wherein X and T are bisarylene.

3. A rhodium hydroformylation catalyst containing bisphosphite ligands of the formula I as defined in claim 1, wherein X and T are radicals of the formula

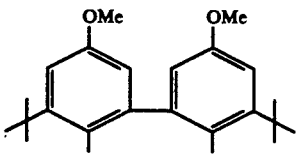

and R$^2$ is o-phenylene, 2,2-dimethyl-1,3-propylene or 1,1,2,2-tetramethylethylene.

4. A rhodium hydroformylation catalyst containing bisphosphite ligands of the formula I as defined in claim 1, where X and R$^2$, independently of one another, are o-phenylene, 2,2-dimethyl-1,3-propylene or 1,1,2,2-tetramethyl-ethylene and T is o-phenylene.

5. A rhodium hydroformylation catalyst containing bisphosphite ligands of the formula I as claimed in claim 1, wherein T is the radical of the formula

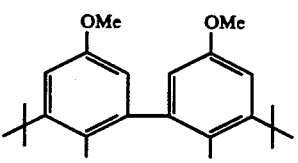

and X and R$^2$, independently of one another, are o-phenylene, 2,2-dimethyl-1,3-propylene or 1,1,2,2-tetramethylethylene.

6. A rhodium hydroformylation catalyst containing bisphosphite ligands as defined in claim 5, wherein T is o-phenylene.

* * * * *

UNITED STATES PATENT AND TRADEMARK OFFICE
CERTIFICATE OF CORRECTION

PATENT NO. : 5,202,297

DATED : April 13, 1993

INVENTOR(S) : LORZ et al.

It is certified that error appears in the above-identified patent and that said Letters Patent is hereby corrected as shown below:

Claim 5, Column 12, Line 27:
        That part reading "claimed" should read -- defined --

Signed and Sealed this

Eleventh Day of January, 1994

*Attest:*

BRUCE LEHMAN

*Attesting Officer*     *Commissioner of Patents and Trademarks*